United States Patent [19]

Toy et al.

[11] 4,075,073
[45] Feb. 21, 1978

[54] METHOD FOR THE PREPARATION OF BIS(PERFLUORO-T BUTYL) PEROXIDE

[75] Inventors: Madeline S. Toy, Palo Alto; Roger S. Stringham, Woodside, both of Calif.

[73] Assignee: The United States of America as represented by the Secretary of the Air Force, Washington, D.C.

[21] Appl. No.: 771,858

[22] Filed: Feb. 23, 1977

[51] Int. Cl.² .............................................. B01J 1/10
[52] U.S. Cl. ............................................. 204/158 R
[58] Field of Search ................................... 204/158 R

[56] References Cited

U.S. PATENT DOCUMENTS

| 2,967,810 | 1/1961 | Harris | 204/158 R |
| 3,151,051 | 9/1964 | Braid et al. | 204/158 R |

Primary Examiner—Howard S. Williams
Attorney, Agent, or Firm—Joseph E. Rusz; William J. O'Brien

[57] ABSTRACT

A method for synthesizing bis(perfluoro-t-butyl) peroxide through the photolysis of perfluoro-t-butyl hypofluorite in the presence of tetrafluorohydrazine.

2 Claims, No Drawings

METHOD FOR THE PREPARATION OF BIS(PERFLUORO-T BUTYL) PEROXIDE

STATEMENT OF GOVERNMENT INTEREST

The invention described herein may be manufactured and used by or for the Government for governmental purposes without the payment of any royalty thereon.

BACKGROUND OF THE INVENTION

This invention relates to bis(perfluoro-t-butyl) peroxide and to a method for its preparation. More particularly, this invention concerns itself with a method for producing bis(perfluoro-t-butyl) peroxide that results in the production of high yields of the pure peroxide as well as a useful by-product without the attendant separation problems associated with prior art methods of preparation.

Perfluoroalkyl peroxides are well known for a wide variety of applications in the chemical, aircraft, space and mining industries. A peroxide of this class that is of particular interest is bis(perfluoro-t-butyl) peroxide. It possesses the following structural formula:

$$(CF_3)_3COOC(CF_3)_3 \tag{1}$$

and has been found to be particularly useful as a thermally stable crosslinking agent for unsaturated fluoropolymers. It is also useful as a source of free radicals for polymer initiation, ignition acceleration and as an intermediate in organic synthesis. However, previous methods of preparation often provided low yields as well as undesirable reaction by-products.

In an attempt to overcome the problems associated with previous methods of preparing bis(perfluoro-t-butyl) peroxide, it was found that a free radical condition could be created photolytically and thermally. To be more specific, under photolysis, the homolysis of the bond in perfluoro-t-butyl hypofluorite was found to take place in the presence of tetrafluorohydrazine. The hydrazine component serves as a radical scavenger. This reaction may be presented by the equation:

$$(CF_3)_3COF + N_2F_4 \rightarrow (CF_3)_3COOC(CF_3)_3 + NF_3 \tag{2}$$

The method represented by equation (2) produces a high yield of the pure peroxide in the absence of separation problems, since the inert volatile $NF_3$ is readily evacuated at $-90°$ C to leave a pure bis(perfluoro-t-butyl) peroxide residue.

SUMMARY OF THE INVENTION

In the present invention, bis(perfluoro-t-butyl) peroxide is synthesized from a reaction medium composed of perfluoro-t-butyl hypofluorite and tetrafluorohydrazine. The reaction takes place under photolysis. The product of the reaction is then evacuated at $-90°$ C to remove the by-product ($NF_3$) leaving a pure $(CF_3)_3COOC(CF_3)_3$ residue.

Accordingly, the primary object of this invention is to provide a novel method for preparing bis(perfluoro-t-butyl) peroxide.

Another object of this invention is to provide a novel method for producing bis(perfluoro-t-butyl) peroxide that gives high yield of the pure peroxide in the absence of separation problems and also provides a useful by-product of $NF_3$.

The above and still other objects and advantages of the present invention will become more readily apparent upon consideration of the following detailed description of its preferred embodiments.

DESCRIPTION OF THE PREFERRED EMBODIMENTS

In accordance with this invention, it has been found that the above-described objects can be accomplished by effecting a photolytic reaction between equimolar amounts of perfluoro-t-butyl hypofluorite and tetrafluorohydrazine. The resulting volatile reaction product, $NF_3$, is evacuated at $-90°$ C leaving a pure bis(perfluoro-t-butyl) peroxide residue.

The method of this invention resulted from a line of research that concerns itself with the nature of O-F bond dissociations by homolytic and heterolytic fissions.

The heterolytic cleavage of the O-F bond was previously known. The dissociation of the O-F bond was confirmed in accordance with this invention, not only by homolysis, but also by hererolytic cleavage from the reactants (perfluoro-t-butyl hypofluorite $(CF_3)_3$ COF AND tetrafluorohydrazine $N_2F_4$), which are subjected to photolytic or free radical and thermal or ionic reaction.

The free radical conditions are created photolytically. Under photolysis, the homolysis of the O-F bond $$(CF_3)_3COF \rightarrow (CF_3)_3CO\cdot + F\cdot \tag{3}$$

has been demonstrated in the presence of $N_2F_4$ ($D_{F_2N\text{-}NF_2} = 21.7$ kcal), which dissociates into $NF_2$ radical to function as the fluorine atom acceptor, $$2(CF_3)_3COF + \tag{4}$$

$$N_2F_4 \xrightarrow[90°\text{ C}]{200\text{ watt, quartz}} (CF_3)_3COOC(CF_3)_3 + 2NF_3 \uparrow$$

The likely intermediate $(CF_3)_3 CONF_2$ was not detected, and the inert volatile $NF_3$ (confirmed by ir) was readily evacuated at $-90°$ C to leave a pure $(CF_3)_3COOC(CF_3)_3$ residue. The structure of the peroxide was confirmed by ir in accordance with the literature, by 19F nmr (a single resonance at 69.7 ppm relative to external $CFCl_3$ and by a field ionization mass spectrum of one peak at a mass m/e value of 470.

The ionic (i.e., anionic) condition which permits the reaction of this invention to come to completion is created by the presence of the cation-forming $N_2F_4$ reactant. This condition was known to form the stable $N_2F_5^+ASF_6^-$, Salt in the presence of $A_sF_5$ at $-78°$ C. This information initiated an investigation of whether $N_2F_4$ might function as a fluoronium ion accepter in the presence of neat $(CF_3)_3COF$ to demonstrate the heterolytic cleavage and generation of the fluoronium ion as shown in the following equation:

$$(CF_3)_3COF (CF_3)_3CO^- + F^+ \tag{5}$$

It was found that $(CF_3)_3COF$ reacts with $N_2F_4$ at $-60°$ C to form a white solid salt, m.p. about 150° C, in accordance with the following equation:

$$(CF_3)_3COF + N_2F_4 \xrightarrow{-60°\text{ C}} (CF_3)_3CO\ N_2F_5^+ \tag{6}$$

The pentafluorohydrazinium perfluoro-t-butoxide product of equation (6) is stable at ambient temperature in an evacuated reaction vessel for several days to several months. However, brown fumes evolve under agitation. These fumes may be due to a secondary reaction with the container (Pyrex or quartz). The salt is soluble in anhydrous hydrogen fluoride and crystallizes upon evacuation of the solvent. The ir spectrum (as KCl pellet using AgCl windows under anhydrous condition) shows the presence of $CF_3$ and NF absorptions, as expected; whereas, the low temperature $^{19}F$ nmr analysis (at $-80°$ C in HF solvent, using a perfluorinated ethylene-propylene copolymer nmr tube) shows only one peak from $(CF_3)_3CO$-group (149 ppm to external standard $CFCl_3$) with almost unobservable NF peaks from pentafluorohydrazinium cation (i.e., $N_2F_5^+$ portion of the sale). The mass spectrum of the salt of equation (6) shows NF fragments ($N_2F_4^+$, $N_2F_3^+$, $NF_3^+$, $NF_2^+$) from the $N_2F_5^+$ portion of the molecule, but no anion $(CF_3)_3CO^-$ fragments were detected due to the negatively charged ion. The barely detectable $N_2F_5^+$ portion of salt in the $^{19}F$ nmr spectrum can be explained by the rapid exchange reaction that occurred between the salt and HF solvent. The solution of the salt also shows strong esr signals to indicate the generation of free radical species in HF solvent.

However, when the same reactants, that is, the perfluoro-t-butyl hypofluorite and tetrafluorohydrazine are subjected to photolysis for about 1 hour at $-90°$ C under a 200 watt quartz lamp, a very pure bis(perfluoro-t-butyl) peroxide residue remains after the $NF_3$ volatile by-product is evacuated at $-90°$ C. Equation (4) set forth hereinbefore, demonstrates the method of this invention.

Perfluoro-t-butyl hypofluorite (0.69 g) was prepared by direct fluorination of the sodium salt of perfluoro-t-butanol (0.70 g) at 23° C. The purity of the liquid product was confirmed from its IR and $^{19}F$ NMR spectra as described by Frager and Thompson for $(CF_3)_3COF$.

Perfluoro-t-butanol was obtained from PCR, Inc. This reagent was checked by means of IR and $^{19}F$ NMR spectroscopic methods and was freed from noncondensible impurities before use by condensation and pumping under vacuum (0.1 mmHg) in a trap cooled with liquid nitrogen.

All compounds were handled in copper, stainless steel quartz or Pyrex reaction vessels attached to a copper vacuum manifold system equipped with Monel valves and Cajon Ultratorr fittings. Pressures were measured by means of Ashcroft gauges to 5 atm and by means of a Pennwalt Wallace and Tiernan gauge (0–1550 mmHg) which is accurate to 0.15 mmHg. Amounts of volatile reactants were determined by P-V-T measurements assuming ideal gas behavior.

The IR spectra were measured on a Perkin-Elmer 467 spectrometer with a 5 cm Monel gas cell equipped with AgCl windows. Liquid and solid samples were measured as thin films between AgCl windows. The $^{19}F$ NMR spectra were determined by means of a Varian XL-100 spectrometer operating at 94.1 MHz, using $CFCl_3$ as an external reference at 30° C. Mass spectra were obtained using an LKB 9000 mass spectrometer which has an ionizing potential of 70 eV and a resolving power of 2000. The gas chromatograph-mass spectra were also run on the LKB 9000 instrument using a 3 m × 2 mm glass column packed with 1 percent SE-30 on Gas-Chrom Q at 50° C and ca. 1 to 3 nitrogen carrier gas pressure. Elemental analyses were obtained by means of a double-focusing high-resolution mass spectrometer.

From a consideration of the foregoing, it can be seen that the present invention provides a simple, economical and efficient method for preparing bis(perfluoro-t-butyl) peroxide. This material finds utility in a wide variety of applications in the chemical industry, and has been found to be especially useful as a thermally stable cross-linking agent for unsaturated fluoropolymers and as a source of free radicals for polymer initiation.

While the invention has been described with particularity in reference to specific embodiments thereof, it is to be understood that the disclosure of the present invention is for the purpose of illustration only and is not intended to limit the invention, the scope of which is defined by the appended claims.

What is claimed is:

1. A method for preparing bis(perfluoro-t-butyl) peroxide which comprises the steps of (A) forming a reaction mixture of (1) perfluoro-t-butyl hypofluorite and (2) tetrafluorohydrazine; (B) subjecting said mixture of reactants to photolysis for a period of time and at a temperature sufficient to effect a reaction therebetween; and (C) separating the resultant reaction products.

2. A method in accordance with claim 1 wherein said photolysis is induced by a 200 watt quartz lamp for a period of about one hour and said reaction products are separated by evacuation at about $-90°$ C.

* * * * *